(12) United States Patent
Bailey et al.

(10) Patent No.: US 8,882,821 B2
(45) Date of Patent: Nov. 11, 2014

(54) CARTRIDGE DELIVERY SYSTEM FOR DELIVERY OF MEDICAL DEVICES

(75) Inventors: F. Kristen Bailey, Bloomington, IN (US); Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1200 days.

(21) Appl. No.: 12/114,309

(22) Filed: May 2, 2008

(65) Prior Publication Data
US 2009/0276028 A1 Nov. 5, 2009

(51) Int. Cl.
*A61F 2/06* (2013.01)
*A61F 2/95* (2013.01)

(52) U.S. Cl.
CPC ........................................ *A61F 2/95* (2013.01)
USPC .......................................................... 623/1.12

(58) Field of Classification Search
USPC .......................... 128/898; 606/108, 194, 200; 623/1.1–1.14, 1.23, 902–903; 206/438
See application file for complete search history.

(56) References Cited

U.S. PATENT DOCUMENTS

| | | |
|---|---|---|
| 3,657,744 A | 4/1972 | Ersek |
| 4,572,186 A | 2/1986 | Gould et al. |
| 5,104,399 A | 4/1992 | Lazarus |
| 5,453,090 A * | 9/1995 | Martinez et al. ............... 606/108 |
| 5,571,166 A * | 11/1996 | Dinh et al. ..................... 128/898 |
| 5,693,088 A | 12/1997 | Lazarus |
| 5,800,517 A | 9/1998 | Anderson et al. |
| 5,817,100 A | 10/1998 | Igaki |
| 5,833,694 A | 11/1998 | Poncet |
| 6,117,140 A | 9/2000 | Munsinger |
| 6,126,685 A | 10/2000 | Lenker et al. |
| 6,858,034 B1 | 2/2005 | Hijlkema et al. |
| 6,926,732 B2 | 8/2005 | Derus et al. |
| 7,137,993 B2 | 11/2006 | Acosta et al. |
| 7,314,481 B2 | 1/2008 | Karpiel |
| 7,316,708 B2 | 1/2008 | Gordon et al. |
| 2005/0165352 A1* | 7/2005 | Henry et al. .................. 604/108 |
| 2005/0218022 A1* | 10/2005 | Cervantes ..................... 206/363 |
| 2006/0115449 A1* | 6/2006 | Pacetti ....................... 424/78.27 |
| 2007/0043430 A1* | 2/2007 | Stinson ........................ 623/1.15 |
| 2007/0061008 A1* | 3/2007 | Salahieh et al. ............. 623/2.11 |
| 2007/0265694 A1* | 11/2007 | Sarac et al. .................. 623/1.11 |
| 2008/0147082 A1* | 6/2008 | Pynson .......................... 606/107 |

FOREIGN PATENT DOCUMENTS

WO WO 00/32136 A1 6/2000

* cited by examiner

*Primary Examiner* — Ashley Fishback
(74) *Attorney, Agent, or Firm* — Brinks Gilson & Lione

(57) ABSTRACT

A delivery cartridge, delivery system and a method for delivering a medical device are provided. The delivery cartridge includes a housing having a proximal end, a distal end and a cavity defined therein. The delivery cartridge further includes a proximal end covering member connected to the proximal end, a distal end covering member connected to the distal end, and a medical device positioned within the cavity. The housing is adapted to fit within a lumen of a delivery system.

18 Claims, 7 Drawing Sheets

CARTRIDGE DELIVERY SYSTEM FOR DELIVERY OF MEDICAL DEVICES

TECHNICAL FIELD

The present invention relates to medical devices, and in particular to delivery cartridges, systems for delivering medical devices to a body site and methods of deploying the medical devices within the body site.

BACKGROUND

A wide variety of implantable medical devices may be delivered to a patient using a delivery system to transport the device to an implant position within a bodily lumen. For example, the device may be delivered to the vasculature by employing the Seldinger technique or related percutaneous entry techniques. For some implantable medical devices, delivery may be accomplished using an endoscope for intraluminal delivery.

Such systems typically utilize a wire guide inserted into the lumen to extend to the site of implantation of the medical device such as a stent, stent graft, filter, occluder, valve or the like. An introducer sheath is placed over a portion of the wire guide and a catheter inserted over the wire guide within the introducer sheath. The medical device is contained within a distal portion of the sheath until delivery to the site of implantation. The medical device is then released from the catheter distal tip and deployed. The insertion and delivery procedure are monitored closely through fluoroscopy, angiograms, ultrasound or CT scanning or the like. Radiopaque or echogenic markers are commonly used as landmarks on the guide wire, catheter and medical device to assure eventual accurate positioning of the device at the site of implantation and its full deployment.

Typically, the medical device may be positioned within the delivery catheter prior to the delivery to the physician. Some medical devices may require hydration prior to use that makes prepackaging of the device within the delivery catheter more difficult. In some situations, the medical device may be hydrated just prior to the patient in the operating room which requires manipulation of the medical device by the medical personnel. In other situations, more than one medical device may be needed or a different type of medical device than originally provided with the catheter may be desirable.

What is needed is a delivery cartridge that may be provided with a medical device therein that allows the medical device to be provided with a delivery catheter or separately therefrom and loaded into the delivery catheter at the site of the medical procedure. The medical device may also be provided in a hydrated state.

SUMMARY OF THE INVENTION

Accordingly, it is an object of the present invention to provide a cartridge, a cartridge delivery system and method having features that resolve or improve on one or more of the above-described drawbacks.

The foregoing object is obtained by providing a delivery cartridge for a medical device. The delivery cartridge includes a housing having a proximal end, a distal end and a cavity defined therein. The delivery cartridge further includes a proximal end covering member connected to the proximal end, a distal end covering member connected to the distal end, and a medical device positioned within the cavity. The housing is adapted to fit within a lumen of a delivery system.

In another aspect, a delivery system for delivering a medical device to a body site is provided. The delivery system includes an outer sheath having a proximal portion, a distal portion and a first lumen extending at least partially through the sheath. The delivery system further includes an inner shaft slidably received within the first lumen; and a delivery cartridge positionable within the distal portion of the first lumen. The delivery cartridge includes a housing including a proximal end, a distal end and a cavity defined within the housing, a proximal end covering member connected to the proximal end, a distal end covering member connected to the distal end. The cavity is configured to receive a medical device for delivery to a delivery site and the inner shaft is configured to slide relative to the outer shaft to deliver the medical device to the delivery site while the housing remains in the first lumen during delivery.

In another aspect, a method of delivering a medical device to a delivery site is provided. The method includes providing a delivery system. The delivery system includes an outer sheath comprising a proximal portion, a distal portion and a first lumen extending at least partially through the sheath, an inner shaft slidably received within the first lumen; and a delivery cartridge positionable within a distal portion of the first lumen. The delivery cartridge includes a housing including a proximal end, a distal end and a cavity defined within the housing, a proximal end covering member connected to the proximal end, a distal end covering member connected to the distal end and a medical device positioned within the cavity. The method further includes advancing the delivery system to a delivery site, deploying the medical device into the delivery site by sliding the inner shaft and the medical device relative to the outer sheath and the housing and withdrawing the inner shaft, the outer sheath and the housing.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION

Figure 1:
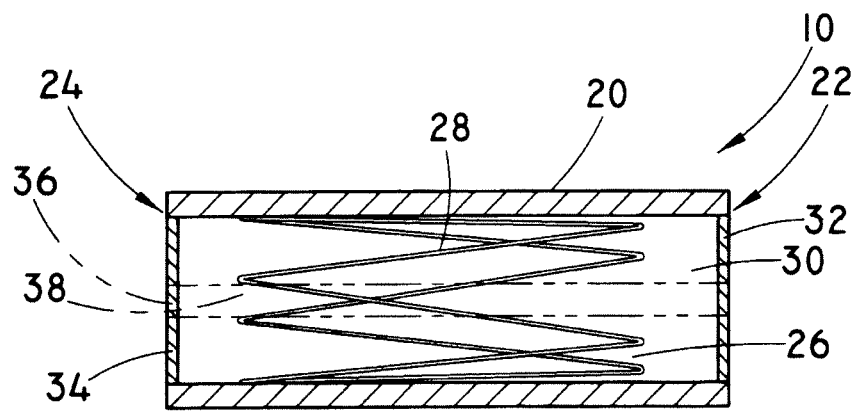
FIG. 1 is a side view of a delivery cartridge of the present invention having a medical device therein.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician operating a delivery system having a medical device therein for insertion into a patient. Hence the term distal means the portion of the device that is farthest from the physician and the term proximal means the portion of the device that is nearest to the physician.

Figure 2:
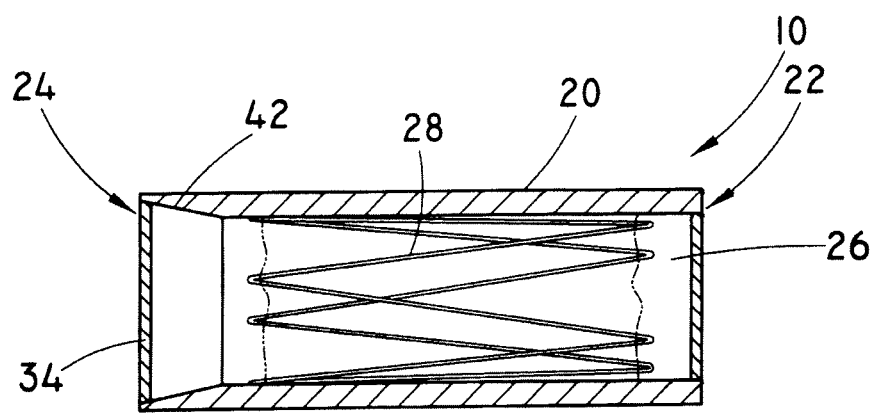
FIG. 2 is a side view of an alternative embodiment of the delivery cartridge shown in FIG. 1

FIGS. 1 and 2 illustrate a delivery cartridge 10 in accordance with embodiments of the present invention. The delivery cartridge 10 shown in FIGS. 1 and 2 includes a housing 20 having a proximal end 22 and a distal end 24. A cavity 26 is defined within the housing 10 between the proximal and distal ends 22, 24 wherein the cavity 26 is configured to receive a medical device 28. The delivery cartridge 10 may further include a lumen 30 extending longitudinally from the proximal end 22 to the distal end 24 (also shown in FIG. 3A-3C). In some embodiments, the cavity 26 of the delivery cartridge 10 may be configured to be sealed for sterility or liquid containment for hydration of the medical device 28. For example, the proximal end 22 may include a proximal covering member 32 and the distal end 24 may include a distal covering member 34 that may be sealed together with the housing 20 so that the delivery cartridge 10 may be sealed. The cartridge 10 may be configured to maintain sterility or hydration or both of the medical device 28 during storage and until delivery of the medical device 28 to the patient. Where the delivery cartridge 10 includes the lumen 30 therethrough, the delivery cartridge 10 may also provide a sealed cavity 26 for the medical device 28. The proximal covering member 32 and the distal covering member 34 may include openings 36 that are connected to form a lumen 38 through the cavity 26 where the lumen 38 is sealed from the cavity 26.

The medical device 28 may be any medical device that may be delivered to a patient using a catheter delivery system. By way of non-limiting example, the medical devices suitable for delivery using the delivery cartridge 10 may include grafts, stents (self-expandable, balloon expandable and non-expandable), vena cava filters, valves such as heart valves or venous valves, and a variety of other devices having a natural tissue component, a hydration sensitive component a synthetic polymer component or any device not having a biological component. A stent is shown in FIG. 1 as an exemplary medical device. The medical device 28 of FIG. 1 is contained within the cavity 26 of the delivery cartridge 10. The cartridge 10 may include protrusions or frangible elements and the like (not shown) to releasably hold the medical device 28 within the cavity 26. In some embodiments, the medical device 28 may be sized so that the device 28 contacts the housing 20 to position and releasably hold the device 28 in position for delivery in the cavity 26.

Depending on the type of medical device 28 that is being contained within the delivery cartridge 10, the cartridge 10 may include features for facilitating delivery of the medical device 28. For example, as shown in FIG. 2, where the medical device is a self-expanding stent that also may include a biological component connected thereto, the delivery cartridge 10 may include an outwardly tapering distal end 42 so that the stent may expand outward as the stent exits the cartridge 10 for implantation into the patient. The delivery cartridge 10 may be sized and shaped to hold any size medical device 28 that is known to one skilled in the art. The exterior of the housing 20 may be provided in a standard size to be received and fit within the lumen of the delivery device as described below. The dimensions of the cavity 26 may be changed when provided with a standard exterior size housing. For example, the thickness of the walls of the housing may be changed to fit smaller and larger external dimensions for the medical device. Where a smaller medical device 28 is provided, the walls may be extended further into the cavity 26 or an insert may be provided in the cavity 26 so that the overall cavity 26 is appropriately sized and shaped for the medical device 28 contained therein. Similar adjustments may be made internally while providing a standard exterior dimension for the delivery cartridge 10. For example, where a lumen of the delivery device is sized to receive a cartridge having 10 French (Fr) diameter, the cartridge 10 may be configured to provide a medical device 28 having a non-expanded exterior dimension less than 10 Fr. The cartridge 10 may contain any size medical device 28 for example 5 Fr and 8 Fr by appropriately sizing the cavity 26. The delivery cartridge 10 may be provided in a plurality of outer diameters so that the delivery cartridge may be loaded into any size delivery system in the operating room, depending on the needs of the patient.

Figure 3A:
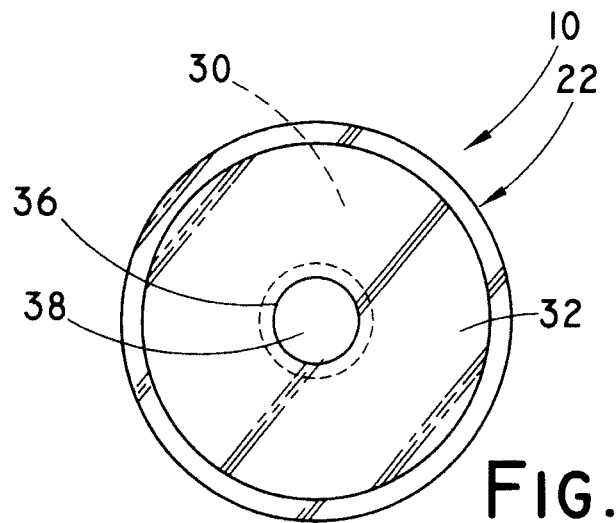
FIG. 3A is an end view of the delivery cartridge shown in FIG. 1.
Figure 3B:
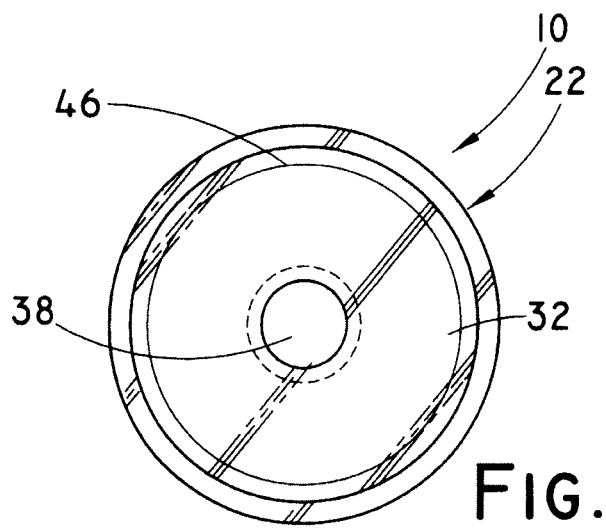
FIG. 3B is an alternative end view of the cartridge shown in FIG. 3A.
Figure 3C:
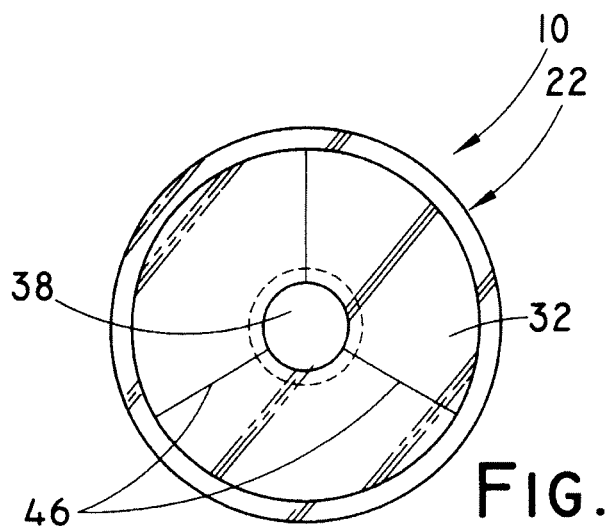
FIG. 3C is an alternative end view of the cartridge shown in FIG. 3A.

As described above, the delivery cartridge 10 may include proximal and distal covering members 32 and 34. By way of example, the proximal covering member 32 is shown in FIGS. 3A-3C. The distal covering member 34 may be the same as the proximal covering member 32, but may also be different. FIG. 3A illustrates the proximal covering member 32 having the opening 36 and the lumen 38 extending therethrough. The proximal covering member 32 may be configured to allow the end 22 to be opened for delivery of the medical device to the patient. Any suitable material(s) may be used for the proximal and distal covering members 32, 34 that allow opening or tearing of the members 32, 34 for delivery and yet are suitably strong to maintain hydration of the cavity 26 and/or sterility if desired. The members 32, 34 may be scored or punctured to facilitate opening of the ends 22, 24 for delivery of the medical device 28. FIGS. 3B and 3C illustrate frangible portions 46 that may be included on the proximal covering member 32, the distal covering member 34 or both to facilitate opening of the ends 22, 24 for delivery of the medical device 28 as will be explained in greater detail below. The delivery cartridge 10 may also include covering member 32, 34 that are impenetrable and are removed prior to loading the cartridge 10 in the delivery system 100.

The housing 20 of the delivery cartridge 10 may be made from any suitable material(s) known to one skilled in the art. The material(s) forming the housing 20 should be suitably rigid or semi-rigid to protect and maintain the shape of the medical device 28 within the housing 20 during storage and delivery to the patient. The material(s) forming the housing 20 should also be compatible with the hydration and/or sterility procedures if such procedures are used with the delivery cartridge 10.

The delivery cartridge 10 may be provided in a plurality of sizes, either as a separate entity or together with a delivery system. The delivery cartridge 10 may be configured to provide a hydrated environment for the medical device that may be delivered to the physician in an already hydrated state, either within the delivery system or separately. In some embodiments, the medical device 28 may be provided in a dehydrated condition within the delivery cartridge and delivered to the physician. The delivery cartridge 10 may be used as a container to hydrate the medical device just prior to use, before or after positioning the delivery cartridge 10 in the lumen 112. The delivery cartridge 10 may also be provided with a sterile medical device contained therein. The delivery cartridge 10 may be provided within separate packaging or may be provided as the packaging itself, having a sterile cavity 26 with in the cartridge 10. The medical device 28 may also include radiopaque or echogenic markers of the like to help delivery and positioning of the medical device 28 in the patient. The delivery cartridge 10 may also be provided with indicia on the cartridge to indicate sterility, expiration, sizing and the like of the contents within the packaging.

Figure 4:
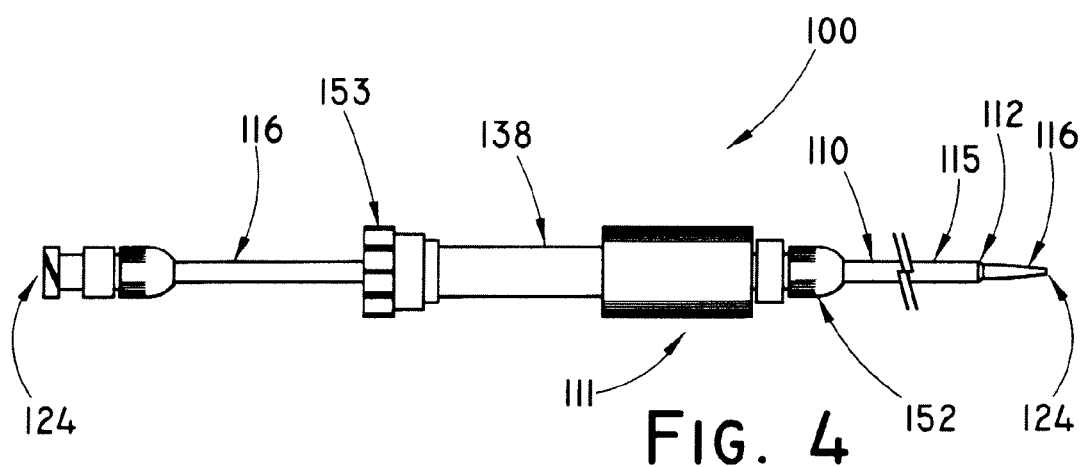
FIG. 4 is a top view of a delivery system.

FIG. 4 illustrates an exemplary delivery system 100 that may be used to deliver the medical device 28 within the delivery cartridge 10 to the site of implantation within the patient. The delivery system 100 may be any kind of delivery system suitable for delivery of medical devices to an interior bodily location in a patient. The exemplary delivery system 100 shown in FIG. 4 includes an outer delivery sheath 110, having a sheath lumen 112 (shown in FIG. 5) through which an inner shaft 116 may be inserted. An inner shaft lumen 124 may extend through the inner shaft 116. The lumen 112 is configured to receive the delivery cartridge 10 therein. The delivery system 100 may further include a luer connector hub 152 at a proximal end 111 of the sheath 110. A connector 138 connected to the connector hub 152 connects to the inner shaft 116. A releasably threaded lock 153 at the proximal end of the connector 138 allows releasable locking of the inner shaft 116 in relation to the delivery sheath 110.

Figure 5:
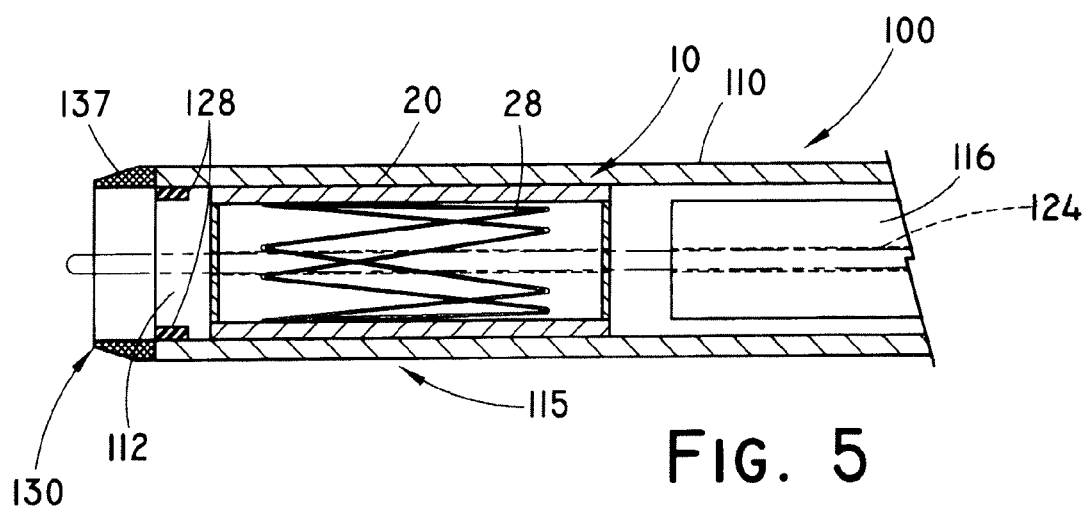
FIG. 5 is a partial sectional view of a distal portion of the delivery system and delivery cartridge.

A partial view of a distal end portion 115 of the delivery system 100 is shown in FIG. 5. In some embodiments, the inner shaft 116 may be a "pusher" catheter configured to push the medical device 28 out of the cartridge 10 and into the delivery site within the patient. As shown in FIG. 5, the delivery cartridge 10 is sized and shaped to fit within the lumen 112 of the outer sheath 110. The outer sheath 110 may further include one or more protrusions 128 that extend into the lumen 112 near the distal tip 130 of the sheath 110. The protrusion 128 may also be a ring-shaped protrusion extending around the interior of the lumen 112 or any shape configured to contact the housing 20 of the delivery cartridge 10. A wire guide may extend through the inner shaft lumen 124 for guiding the delivery system 100 to the delivery site within the patient.

Figure 6A:
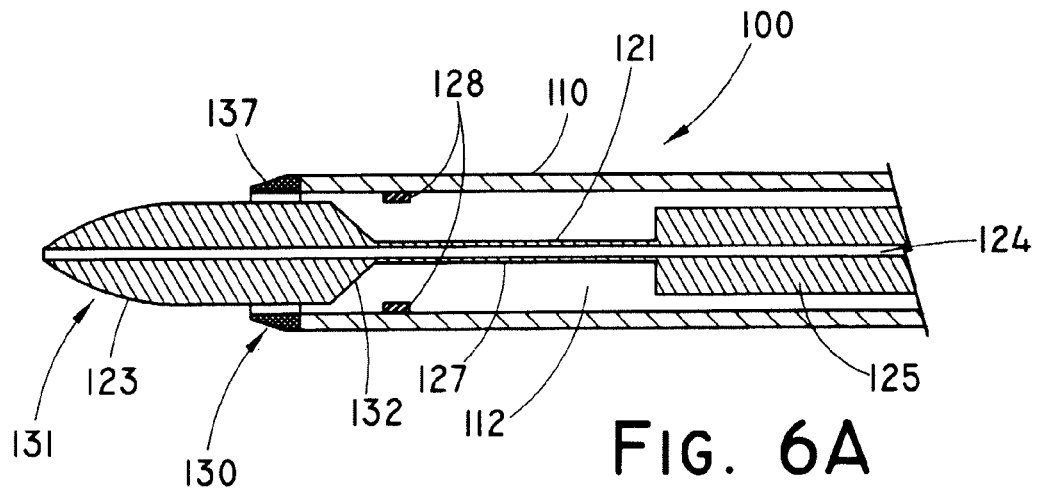
FIG. 6A is a partial, sectional view of an alternative embodiment of the delivery system shown in FIG. 5.
Figure 6B:
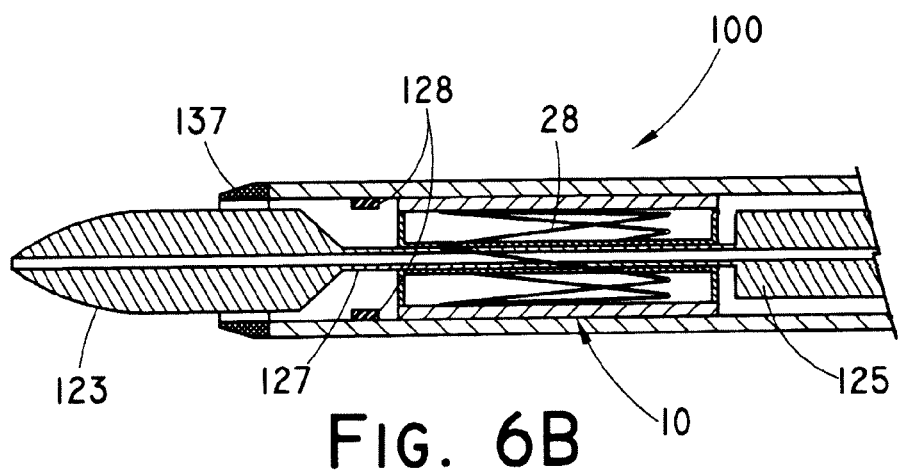
FIG. 6B is a partial, sectional view of the delivery system shown in FIG. 6A with a delivery cartridge.

In some embodiments, an inner shaft 121 may be provided with the delivery system 100 as shown in the partial view of the distal portion of the delivery system 100 in FIG. 6A. The inner shaft 121 is insertable through the lumen 112 of the outer sheath 110 similar to the inner shaft 116. The inner shaft 121 may include a distal tip portion 123, a proximal portion 125 and an intermediate portion 127 disposed between the distal tip portion 123 and the proximal portion 125. The distal end 131 of the distal tip portion 123 may be tapered to facilitate extension of the inner shaft 121 from the lumen 112 of the outer sheath 110 and atraumatic placement of the medical device 28. The proximal portion 132 of the distal tip 123 may also be tapered to provide atraumatic withdrawal of the inner shaft 121 from the delivery site. The intermediate portion 127 of the inner shaft 121 may have a reduced diameter to receive the delivery cartridge 10. The proximal portion 125 may have an increased diameter in relation to the intermediate portion 127 to facilitate delivery of the medical device 28 out of the delivery cartridge 10 and to the delivery site. The medical device 28 is shown in FIG. 6B positioned within the lumen 112 and on the intermediate portion 127 of the inner shaft 121. In some embodiments, the outer diameter of the housing 20 of the delivery cartridge 10 is dimensioned to be about the same dimension as the outer diameter of the distal tip portion 123. The proximal portion 125 may have a slightly smaller outer dimension so that the proximal portion 125 may push the medical device 28 out of the delivery cartridge 10, leaving the cartridge 10 within the lumen 112 of the outer sheath 110 by retaining the cartridge 10 in the protrusions 128 as will be described in more detail below. The inner shaft 121 may further include the inner shaft lumen 124. A wire guide (not shown) known to those skilled in the art may extend through the inner shaft lumen 124. The delivery system 100 may be configured to include an over the wire delivery system or a rapid exchange delivery system.

The wire guide may be any type of wire guide known in the art suitable for entering tortuous passageways in the body. The wire guide should be sized and shaped to fit and extend at least partially through the inner shaft lumen 124 in the inner shaft 116, 121. In some embodiments, the wire guide may be about 0.035 inch in diameter and about 185 cm in length for a rapid exchange device and up to about 480 cm in length for use with an over the wire device. Other diameters and lengths may be used as these sizes are presented only for illustrative purposes.

The materials used to form the delivery system 100 may be any materials known to one skilled in the art. The delivery system 100 may also include radiopaque or echogenic markers to help position the distal end 115 of the delivery system 100 at the proper delivery site. For example, the outer sheath 110 may include markers 137 at the distal tip 130 for viewing both the sheath 110 and the medical device 28 as the medical device 28 extends distally out of the sheath 110.

In operation, the delivery system 100 may be used to place the medical device 28 supplied within the delivery cartridge 10 in the bodily lumen. As discussed above, the medical device may be deployed within the vasculature or within the gastrointestinal tract. The delivery cartridge 10 provides particular advantages for maintaining hydration, maintaining sterility, supplying a specific size medical device for the needs of a particular patient, on-site loading of the medical device into the delivery system and/or multiple cartridge loadings without removing the outer sheath from the patient.

Figure 7A:
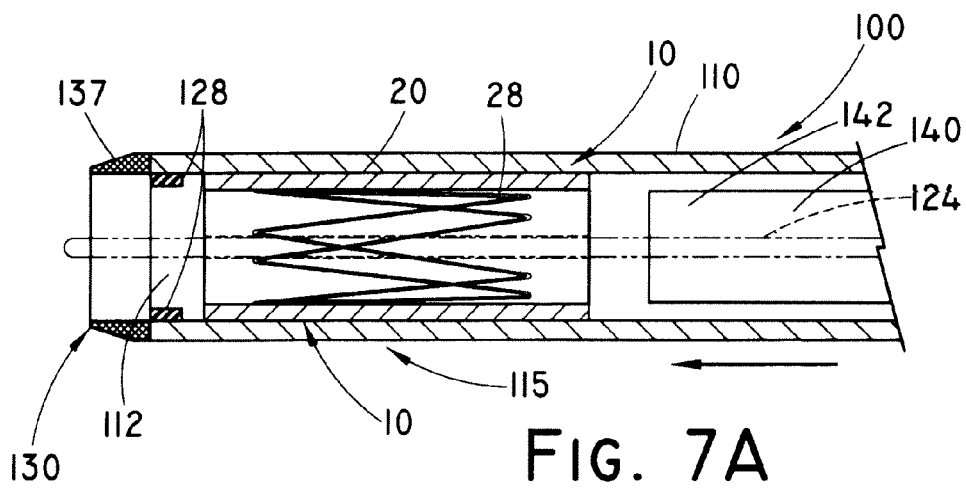
FIGS. 7A to 7C illustrate delivery of the medical device using the delivery system shown in FIG. 5.
Figure 7B:
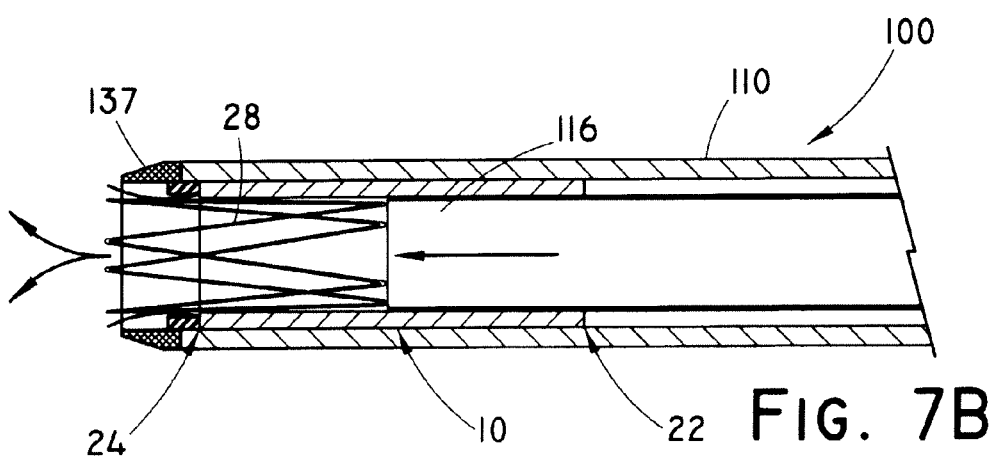
Figure 7C:
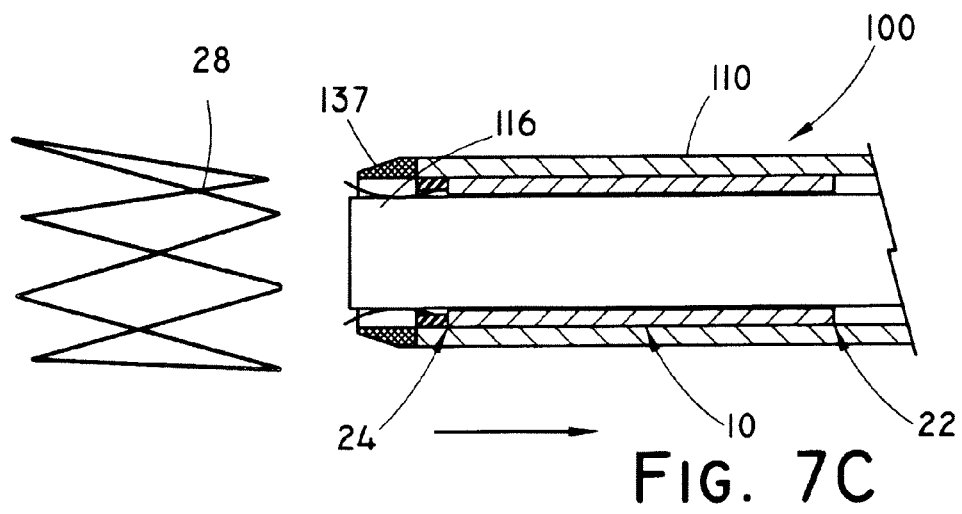

FIGS. 7A to 7C illustrate an exemplary method of delivering the medical device 28 to the patient for implantation. FIG. 7A illustrates the delivery cartridge 10 within the distal portion 115 of the lumen 112 of the outer sheath 110. The delivery cartridge 10 may be positioned within the lumen 112 at the manufacturer or in the operating room. Positioning the delivery cartridge 10 within the lumen 112 in the operating room allows for patient specific selection of the medical device 28 for the specific procedure. In addition, multiple devices 28 may be selected and the cartridges 10 loaded, either sequentially or simultaneously.

In the operating room, the delivery cartridge 10 may be loaded into the lumen 112 before the delivery system is inserted into the patient. For example, the delivery cartridge 10 may be proximally loaded through the proximal end of the lumen 112 of the outer sheath 110 and advanced to the proper position within the sheath 110 for insertion of the delivery device 100 into the patient and subsequent delivery of the medical device 28. A pushing catheter 140 may be used to advance the delivery cartridge 10 into position in the outer sheath 110. The pushing catheter 140 may include a shaft 142 having a diameter that engages the housing 20 of the delivery cartridge 10 so that the entire cartridge 10 is advanced and the medical device 28 within the cavity 26 is not damaged during positioning within the lumen 112. The pushing catheter 140 may be proximally withdrawn from the lumen 112 of the outer sheath 110 and the inner shaft 116 distally advanced within the lumen 112 from the proximal end until the inner shaft 116 is positioned near the cartridge 10. (See FIG. 5.) The delivery cartridge 10 may also be proximally loaded after the outer sheath 110 is positioned within the patient. Additional delivery cartridges 10 may also be proximally loaded during the procedure, if desired, as describe below.

Figure 8A:
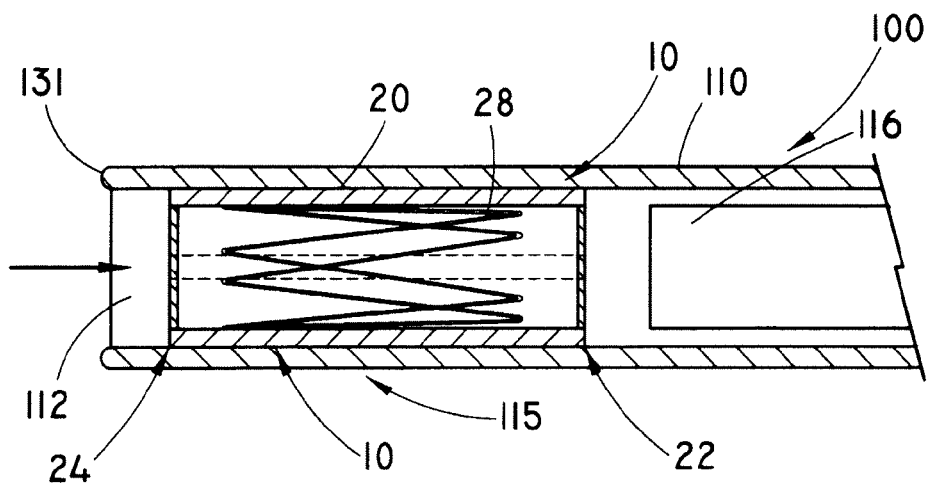
FIGS. 8A and 8B illustrate a partial sectional view of the delivery cartridge being loaded into the delivery system.
Figure 8B:
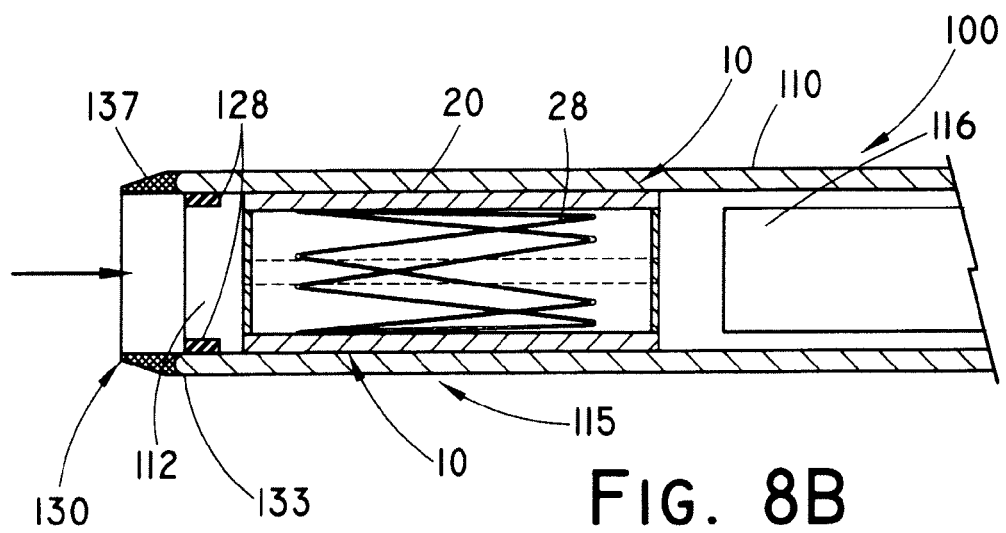

Alternatively, the delivery cartridge 10 may be distally loaded into the distal portion 115 of the lumen 112 of the outer sheath 110 and positioned near the distal tip 130 as shown in FIGS. 8A and 8B. For distal end loading, the distal tip 130 of the outer sheath may be removable for loading so that the protrusions 128 are removable with the distal tip 130 and do not interfere with the advancement of the housing 20 into the lumen 112. As shown in FIG. 8A, the protrusions 128 are removed and the delivery cartridge 10 may be distally inserted into the lumen 112 of the outer sheath 110. After positioning the delivery cartridge 10, the distal tip 130 including the protrusions 128 may be secured to the outer sheath 110 so that the delivery device 100 may be inserted into the patient with the cartridge 10 positioned proximal to the protrusions 128. FIG. 8B illustrates the protrusions 128 and the distal tip 130 reconnected to the outer sheath 110. A connector 133 may be included to removably connect the distal tip 130 to the outer sheath 110. The inner shaft 116 may be positioned within the lumen 112 of the outer sheath 110 either before or after distal loading of the cartridge 110.

Delivery of the medical device 28 to the delivery site within the patient may be accomplished by inserting the distal end portion 115 of the delivery device 100 into the patient. The delivery device 100 may be advanced over a wire guide according to standard procedures. Once the delivery device is properly position for delivery of the medical device 28 to the patient and the delivery cartridge 10 is position within the lumen 112, the inner shaft 116 may be distally advanced within the lumen 112.

As shown in FIG. 7B, the inner shaft 116 is sized and shaped to advance through the proximal end 22 of the delivery cartridge 10 to contact the medical device 28 and distally advance the medical device 28. The inner shaft may also be sized so that the housing 20 of the cartridge 10 remains within the lumen 112. As shown in FIG. 7B, the protrusions 128 hold the cartridge 10 within the lumen 112 while the medical device itself is advanced. As discussed above, the covering members 32, 34 may include frangible portions 46 that are broken as the inner shaft 116 advances distally, pushing through the proximal covering member 32 and the medical device 28 pushes through the distal covering member 34. In some embodiments, the proximal covering member, the distal covering member 34 or both may be removed before the delivery system 100 is inserted into the patient. For example, the distal covering member 34 may be removed just prior to inserting the delivery system 100 into the patient by pulling off the covering member 34 through the distal tip 130 or by manually puncturing the distal covering member 34. By releasing the distal covering member 34 before advancement of the medical device 28, the medical device 28 does not get damaged by distal advancement through the distal covering member 34. The proximal covering member 32 may be punctured by the inner shaft 116. Advancement of the medical device 28 may also be accomplished by retracting the outer sheath 110 in relation to the inner shaft 116.

The medical device 28 may be advanced until the medical device is implanted at the delivery site. In some embodiments, the medical device 28 may be a self-expanding stent that expands to the delivered size once the device 28 exits the distal tip 130 of the outer sheath 110. As shown in FIG. 7C, the inner shaft 116 may be retracted into the outer sheath 110 or the sheath 110 may be advanced over the inner shaft 116 and the delivery device 100 removed from the patient. Where a subsequent medical device is to be delivered to a patient, the sheath 110 may remain in the patient and the inner shaft 116 and the delivery cartridge 10 may be removed from the lumen 112 by proximally retracting the shaft 116. The shaft 116 may include devices for capturing the empty cartridge 10 for removal, such as expansion members (not shown) that may be expandable by the user to protrude into the housing 20 for removal. A subsequent cartridge 10 having a medical device 28 therein may be proximally loaded into the lumen 112 of the outer sheath 110 as described above. As will be understood by one skilled in the art, the delivery cartridge 10 is configured to be easily slidable with in the lumen 112 and provides a low friction method for placing the medical device within the delivery system. The method of delivery may be repeated as many times are required and in several different delivery locations.

Figure 9:
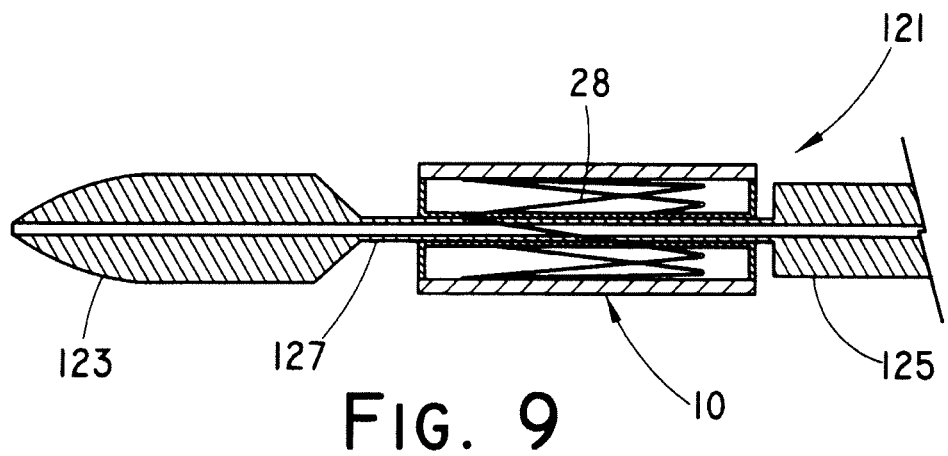
FIG. 9 is a side view of the delivery cartridge on the inner shaft of the delivery system.

The inner shaft 121 shown in FIGS. 6A and 6B may be particularly useful for delivery of balloon expandable devices. The delivery cartridge 10 may be loaded onto the intermediate portion 127 that also includes a balloon (not shown). Similar to the delivery of the cartridge 10 using the inner shaft 116, the inner shaft 121 may be used for placement of the medical device at the implantation site. The inner shaft 121 may be moved relative to the outer sheath 110 for positioning the medical device. For example, the distal end 123 of the inner shaft 121 and the intermediate portion 127 having the medical device mounted thereon may be advanced passed the protrusions 128 so that the housing 20 of the cartridge 10 remains in the lumen 112 of the outer sheath 110. With the medical device in position in the patient, a balloon may be expanded to expand and implant the medical device 28 in the patient. The intermediate portion 127 and the distal end 123 of the inner shaft 121 may be proximally retracted into the lumen 112. A subsequent medical device 28 may also be delivered using the inner shaft 121, for example by providing a new inner shaft 121 having a delivery cartridge loaded thereon. The first inner shaft 121 could be completely removed and the second inner shaft 121 be advanced distally through the lumen 112 of the outer sheath 110. The delivery cartridge 10 may be provided with the inner sheath 121 to protect the medical device 28 as described above and as shown in FIG. 9.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. Application of the principles of the invention to any lumens or vessels within the body of a patient, including areas within the digestive tract such as the pancreatic system, as well as areas outside the digestive tract such as other vascular systems, by way of non-limiting examples, are within the ordinary skill in the art and are intended to be encompassed within the scope of the attached claims.

The invention claimed is:

1. A delivery system for delivering a medical device to a body site, the system comprising:
   an outer sheath comprising a proximal portion, a distal portion and a first lumen extending at least partially through the sheath;
   an inner shaft slidably received within the first lumen; and
   a delivery cartridge separable from and positionable within a distal portion of the first lumen, the delivery cartridge comprising:
      a housing including a proximal end, a distal end, a sealed cavity defined within the housing and a housing lumen extending between the proximal end and the distal end of the housing, the housing lumen being separate and sealed from the cavity;
      a proximal end covering member connected to the proximal end;
      a distal end covering member connected to the distal end, the housing, the proximal end covering member and the distal end covering member together forming the sealed cavity; and
      a medical device positioned within the sealed cavity of the housing;
   wherein the inner shaft is configured to slide relative to the outer sheath to deliver the medical device to the delivery site while the distal end of the housing remains in the first lumen during delivery.

2. The delivery system of claim 1, wherein the medical device within the cavity is sterile.

3. The delivery system of claim 1, wherein at least one of the proximal end covering member or the distal end covering member comprises a frangible portion.

4. The delivery system of claim 1, wherein at least one of the proximal end covering member or the distal end covering member is removably connected to the housing.

5. The delivery system of claim 1, wherein the medical device is a stent.

6. The delivery system of claim 1, wherein the medical device comprises a hydratable material.

7. The delivery system of claim 1, further comprising at least one protrusion extending into the first lumen at a distal end portion of the outer sheath, the protrusion configured to retain the housing in the lumen during delivery of the medical device.

8. The delivery system of claim 7, wherein the distal end portion including the at least one protrusion is removably connected to the outer sheath.

9. The delivery system of claim 1, wherein the inner shaft comprises a distal end having a pushing surface, the pushing surface configured to slide within the housing and contact the medical device to push the medical device to the delivery site.

10. The delivery system of claim 1, wherein the inner shaft comprises a distal tip, an intermediate portion and a proximal portion, the intermediate portion configured to receive the medical device and to advance the medical device to the delivery site.

11. The delivery system of claim 1, further comprising a plurality of cartridges positioned within the first lumen.

12. The delivery system of claim 1, further comprising a wire guide insertable through a lumen of the delivery cartridge.

13. The delivery system of claim 1, further comprising a hydrating fluid within the cavity.

14. The delivery system of claim 1, wherein at least one of the proximal end covering member or the distal end covering member comprises a frangible portion.

15. The delivery system of claim 1, wherein the medical device comprises a natural tissue component.

16. A method of delivering a medical device to a delivery site, the method comprising:
   providing a delivery system, the delivery system comprising;
      an outer sheath comprising a proximal portion, a distal portion and a first lumen extending at least partially through the sheath;
      an inner shaft slidably received within the first lumen; and
      a delivery cartridge separate from and positionable within a distal portion of the first lumen, the delivery cartridge comprising:
         a housing including a proximal end, a distal end, a sealed cavity defined within the housing, and a housing lumen extending between the proximal end and the distal end of the housing, the housing lumen being separate and sealed from the cavity;
         a proximal end covering member connected to the proximal end;
         a distal end covering member connected to the distal end; and
         a medical device positioned within the sealed cavity of the housing;
   positioning the delivery cartridge within the distal portion of the first lumen;
   advancing the delivery system to a delivery site;
   deploying the medical device into the delivery site by sliding the inner shaft and the medical device relative to the outer sheath and the housing, the distal end of the housing remaining within the first lumen; and
   withdrawing the inner shaft, the outer sheath and the housing.

17. The method of claim 16 further comprising positioning the delivery cartridge in the distal portion of the first lumen before advancing the delivery system to the delivery site.

18. The method of claim 16 wherein the medical device is deployed by advancing a distal portion of the inner sheath through at least a portion of the housing to advance the medical device out of the housing and to the delivery site.

* * * * *